(12) United States Patent
Crawford et al.

(10) Patent No.: US 12,402,903 B2
(45) Date of Patent: Sep. 2, 2025

(54) MEDICAL RETRIEVAL SYSTEMS, DEVICES, AND RELATED METHODS

(71) Applicant: Boston Scientific Scimed, Inc., Maple Grove, MN (US)

(72) Inventors: Richard Crawford, Galway (IE); Enda Connaughton, Galway (IE); Méabh Holden, Dublin (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/658,053

(22) Filed: May 8, 2024

(65) Prior Publication Data
US 2024/0285297 A1    Aug. 29, 2024

Related U.S. Application Data

(63) Continuation of application No. 17/480,961, filed on Sep. 21, 2021, now Pat. No. 12,004,762.

(60) Provisional application No. 63/084,112, filed on Sep. 28, 2020.

(51) Int. Cl.
*A61B 17/221* (2006.01)
*A61B 17/00* (2006.01)

(52) U.S. Cl.
CPC .. *A61B 17/221* (2013.01); *A61B 2017/00367* (2013.01); *A61B 2017/2212* (2013.01)

(58) Field of Classification Search
CPC ........ A61B 17/221; A61B 2017/00367; A61B 2017/2212; A61B 2017/00287; A61B 2017/00358; A61B 2017/00473; A61B 2017/00477; A61B 17/00234; A61B 2018/1407; A61B 2018/141; A61B 18/1492; A61B 2017/00557; A61B 17/32056; A61B 2017/00867; A61B 17/22031; A61B 10/04
See application file for complete search history.

(56) References Cited

U.S. PATENT DOCUMENTS

| | | | |
|---|---|---|---|
| 5,647,372 A * | 7/1997 | Tovey | A61B 17/00234 600/562 |
| 5,741,271 A * | 4/1998 | Nakao | A61B 18/24 604/523 |
| 5,997,547 A | 12/1999 | Nakao et al. | |
| 8,206,401 B2 | 6/2012 | Nakao | |
| 8,652,147 B2 | 2/2014 | Hart | |
| 8,906,036 B2 | 12/2014 | Farascioni | |
| 9,370,341 B2 | 6/2016 | Ceniccola et al. | |

(Continued)

FOREIGN PATENT DOCUMENTS

WO    2016172679 A1    10/2016

*Primary Examiner* — Kathleen S Holwerda
*Assistant Examiner* — Serenity A Miller
(74) *Attorney, Agent, or Firm* — Bookoff McAndrews PLLC

(57) ABSTRACT

In one example, a retrieval device may include a flexible loop; a net coupled to the loop, the net having an opening at least partially circumscribed by the loop; a sheath extending from a proximal end to a distal end; a cord extending through and/or around the net; and a connector assembly movable from a first configuration to a second configuration. In the first configuration, the flexible loop, the net, and the cord may be coupled to the sheath, and in the second configuration, the flexible loop, the net, and the cord may be detached from the sheath.

13 Claims, 3 Drawing Sheets

(56) References Cited

U.S. PATENT DOCUMENTS

| | | | |
|---|---|---|---|
| 11,484,329 B2 | 11/2022 | Ahluwalia et al. | |
| 11,504,103 B2 | 11/2022 | Johnson et al. | |
| 2005/0267492 A1* | 12/2005 | Poncet | A61B 17/221 606/114 |
| 2006/0052799 A1* | 3/2006 | Middleman | A61B 17/320016 606/114 |
| 2008/0221587 A1 | 9/2008 | Schwartz | |
| 2009/0082780 A1 | 3/2009 | Lu et al. | |
| 2012/0046667 A1 | 2/2012 | Cherry et al. | |
| 2013/0190773 A1* | 7/2013 | Carlson | A61B 17/00234 606/114 |
| 2019/0336117 A1* | 11/2019 | Prior | A61B 17/00234 |
| 2020/0305866 A1* | 10/2020 | Knapp | A61B 17/00234 |

* cited by examiner

MEDICAL RETRIEVAL SYSTEMS, DEVICES, AND RELATED METHODS

CROSS-REFERENCE TO RELATED APPLICATIONS

This application is a continuation of U.S. application Ser. No. 17/480,961, filed on Sep. 21, 2021, which claims the benefit of priority from U.S. Provisional Application No. 63/084,112, filed Sep. 28, 2020, each of which is incorporated by reference herein in its entirety.

TECHNICAL FIELD

This disclosure generally relates to medical systems, devices, and related methods that may be used to treat a subject. Aspects of the disclosure relate to medical systems, devices, and methods for endoscopic medical procedures, such as grasping and removing foreign objects from body lumens, organs, or cavities, among other aspects.

BACKGROUND

Organ walls are composed of several layers: the mucosa (the surface layer), the submucosa, the muscularis (muscle layer), and the serosa (connective tissue layer). In gastrointestinal, colonic, and esophageal cancer, lesions or cancerous masses may form along the mucosa and often extend into the lumens of the organs. Polypectomy of colonic polyps has been shown to reduce the risk of colon cancer development. A variety of polypectomy techniques and devices are available, and their use can vary greatly based on local availability and physician preferences. These procedures are generally performed with an endoscope, which is a long, narrow member optionally equipped with a light, imaging equipment, and other instruments. During these procedures, the endoscope may be passed through a percutaneous incision, passed down the throat, or guided through the rectum to reach tissue targeted for resection or dissection. Snare devices are often used in the removal of the targeted tissue, such as polyps, from a patient.

During snaring, the snare may be closed around a polyp to detach the polyp from the patient's body, for example from the colon wall. The loose polyp may then be retrieved by the physician using a net or other device. The physician may insert a net through a working channel of an endoscope and deploy the net around the polyp. Then, the physician may remove the entire endoscope along with the net from the patient's body. During this process, the combination of the polyp and the net may be pulled up to the distal face of the endoscope and the view from a camera at the distal face may be obstructed. When the view of the endoscope is obstructed during withdrawal, the physician may miss cancerous tissue due to the obstructed view. Also, the working channel of the endoscope is occupied by the net retrieval device, and thus cannot be used for other purposes during the withdrawal of the endoscope from the body. If additional polyps are identified, the physician will have to re-insert the endoscope into the patient's body and re-locate the identified polyp for removal, which adds procedural time and additional stress to the patient.

SUMMARY

Examples of the disclosure relate to, among other things, systems, devices, and methods for performing one or more medical procedures with the medical systems and devices. Each of the examples disclosed herein may include one or more of the features described in connection with any of the other disclosed examples.

In one example, a retrieval device may include a flexible loop; a mesh coupled to the loop, the mesh having an opening at least partially circumscribed by the loop; a sheath extending from a proximal end to a distal end; a cord extending through and/or around the mesh; and a connector assembly movable from a first configuration to a second configuration. In the first configuration, the flexible loop, the mesh, and the cord may be coupled to the sheath, and in the second configuration, the flexible loop, the mesh, and the cord may be detached from the sheath.

In other aspects, the retrieval device may include one or more of the following features. The cord may include a slip knot. The retrieval device may also include a drive member coupled to the flexible loop, and the actuation of the drive member may be configured to move the flexible loop relative to the sheath. The drive member may extend through the sheath, and the cord may extend outside of the sheath. The retrieval device may also include a handle including an actuator moveable in a proximal or distal direction relative to a body of the handle, and the actuator may be coupled to the drive member. The application of a proximal puling force onto the drive member may be configured to move the connector assembly from the first configuration to the second configuration. The cord may extend externally from the sheath. The cord may include a free end extending away from the mesh. Upon application of a pulling force on the cord, the cord may be configured to constrict at least a portion of the mesh. Upon constriction of the mesh, the mesh may form a substantially-enclosed bag or sac. The mesh may be configured to remain constricted when the flexible loop, the mesh, and the cord are decoupled from the sheath in the second configuration of the connector assembly. The cord may be woven into the mesh. The cord may be not directly coupled to the flexible loop. The flexible loop may be a snare loop. The connector assembly may include a capsule having a lumen and the flexible loop includes proximal arms that extend into the lumen; and the capsule may be configured to separate from the sheath when the connector assembly moves from the first configuration to the second configuration.

In other aspects, a retrieval device may include a snare loop; a mesh coupled to the snare loop, the mesh having an opening at least partially defined by the snare loop; a sheath extending from a proximal end toward a distal end; a cord extending through and/or around the mesh, and upon application of a pulling force on the cord, the cord is configured to constrict at least a portion of the mesh; and a drive member coupled to the snare loop. The actuation of the drive member may be configured to move the snare loop relative to the sheath.

In other aspects, the retrieval device may include one or more of the following features. The snare loop, the mesh, and the cord may be configured to be decoupled from the sheath. Application of a pulling force on the drive member may be configured to decouple the snare loop, the mesh, and the cord from the sheath.

In other aspects, a method of retrieving an object from a body may include inserting a medical device with a working channel into the body; extending a sheath, and a snare loop and a mesh coupled to the sheath through the working channel and distally of the medical device; placing the mesh around the object; constricting at least a portion of the mesh around the object; and decoupling the snare loop, the mesh, and the object from the sheath. In some examples, the method may further include removing the snare loop, the mesh, and the object from the body separately from the medical device.

It may be understood that both the foregoing general description and the following detailed description are exemplary and explanatory only and are not restrictive of this disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. Proximal and distal directions are labeled with arrows marked "P" and "D", respectively, throughout the figures. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Embodiments of this disclosure include devices, systems, and methods for manipulating, cutting, collecting, retrieving, and/or otherwise carrying tissue. In some examples the devices, systems and/or methods discussed herein may be utilized during endoscopic mucosal resection (EMR), endoscopic submucosal dissection (ESD), polypectomy, and/or other medical procedures. In examples, polypectomy includes endoluminal placement of a retrieval device and a cutting device proximate to a target area within the body of a patient. Placement of the retrieval and cutting devices may be via a catheter, scope (endoscope, bronchoscope, colonoscope, gastroscope, duodenoscope, etc.), tube, or sheath, inserted into the GI tract via a natural orifice or incision. The orifice can be, for example, the nose, mouth, or anus, and the placement can be in any portion of the GI tract, including the esophagus, stomach, duodenum, large intestine, or small intestine. Placement also can be in other organs reachable via the GI tract. A polyp within the body of the patient may be cut by the cutting device for subsequent removal from the patient's body. The retrieval device may collect the polyp and move the polyp out of the patient's body.

Reference will now be made in detail to examples of this disclosure described above and illustrated in the accompanying drawings. Wherever possible, the same reference numbers will be used throughout the drawings to refer to the same or like parts.

Figure 1:
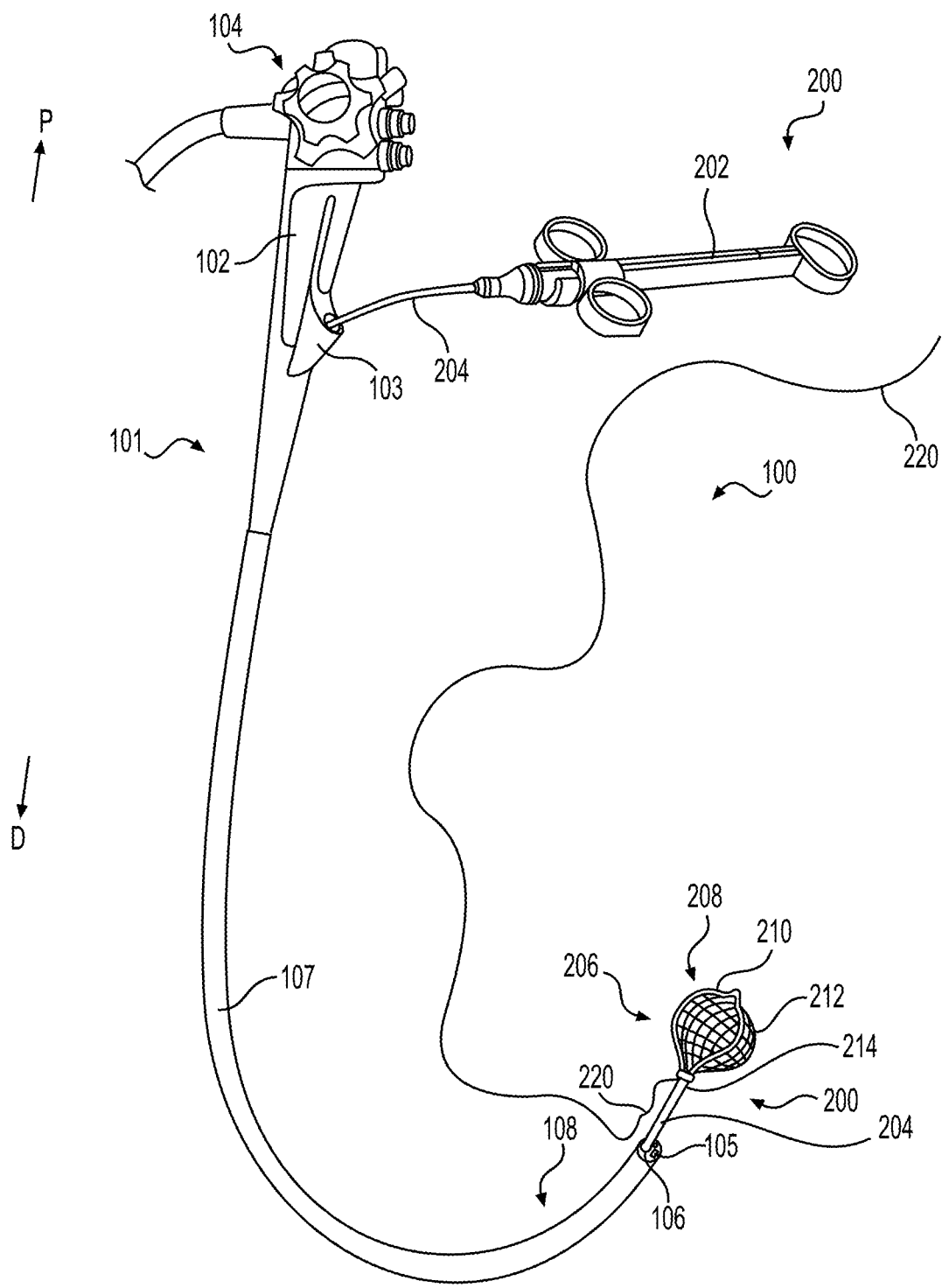
FIG. 1 illustrates a perspective view of a medical device system, according to aspects of this disclosure.

FIG. 1 illustrates a perspective view of an exemplary medical device assembly 100 including an endoscope 101 and a medical device 200. Although medical device assembly 100 is shown with endoscope 101, any other similar insertion device may be used in medical device assembly 100, such as a bronchoscope, colonoscope, gastroscope, duodenoscope, etc. Endoscope 101 may include a handle 102, actuators 104, and a body 107 extending from handle 102 to a distal end 108. A working channel 106 may extend from a working channel port 103 positioned on the handle 102 to an opening at distal end 108. Distal end 108 of endoscope 101 may also include a camera 105, and movement of distal end 108 and functionality of camera 105 may be controlled via one or more actuators 104 on handle 102. Medical device 200 may be configured to be inserted into working channel 106 of endoscope 101.

Medical device 200 may include a handle 202, a main sheath or shaft 204 extending from the handle 202 to a distal portion 206 of medical device 200, and a snare assembly 208 at the distal portion 206 of the device. Main shaft 204 may extend from handle 202 into working channel 106 of endoscope 101, and may be movable within working channel 106. Main shaft 204 may extend longitudinally for a length that is larger than the longitudinal length of endoscope 101, such that once main shaft 204 is pushed through working channel 106, a portion of main shaft 204 extends distally from a distal opening of working channel 106 (shown in FIG. 1). Snare assembly 208 at distal portion 206 of medical device 200 may include a flexible snare loop 210, a net 212, a connector assembly 214, and a cord 220. Cord 220 may be coupled to snare loop 210 and net 212. Cord 220 may extend longitudinally by a length larger than the longitudinal length of endoscope 101, such that once cord 220 is moved through working channel 106, a portion of cord 220 extends distally from a distal opening of working channel 106, while a portion of cord 220 extends proximally out of working channel port 103 (shown in FIG. 1).

Figure 2:
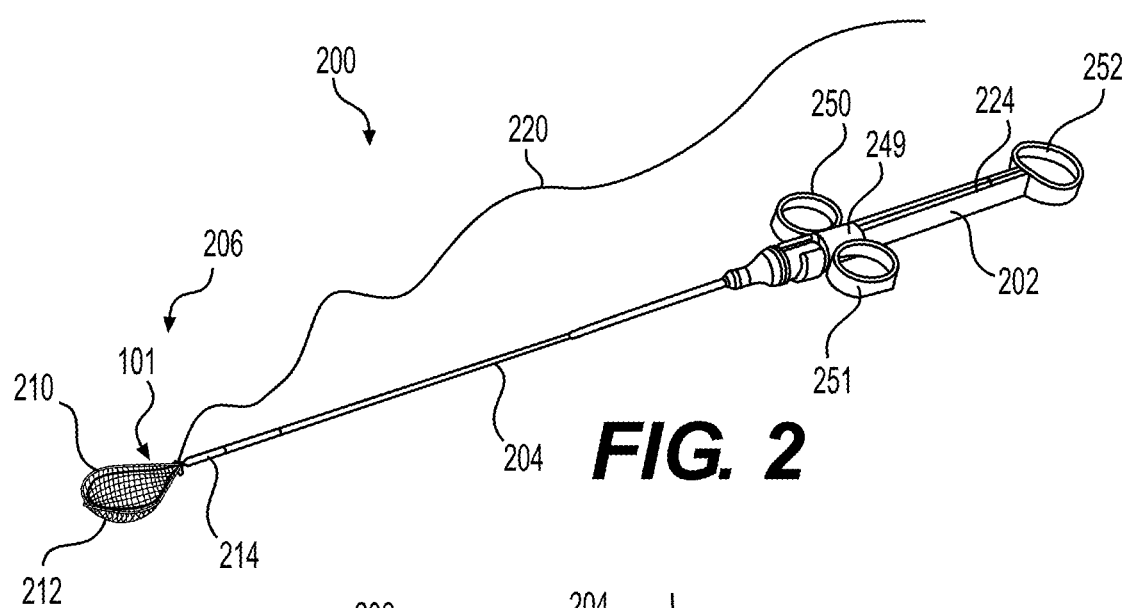
FIG. 2 illustrates a perspective view of an exemplary medical device, according to aspects of this disclosure.

FIG. 2 illustrates a perspective view of medical device 200 from FIG. 1 removed from endoscope 101. Handle 202 may include an actuator 249 including two loops (or holders) 250, 251 configured to receive fingers of an operator of the medical device, and handle 202 may also include a third loop (or holder) 252 at a proximal end of handle 202. Loops 250, 251, and 252 may be rings, grips, or other similar structures that include an aperture to receive one or more fingers of a user. Actuator 249 may be moveably coupled to body 224 of handle 202, and may be configured to slide in distal and proximal directions to move a drive wire 418 (shown in FIG. 4). Drive wire 418 may extend longitudinally from handle 202 through shaft 204 to connector assembly 214, and drive wire 418 may be configured to move snare loop 210 into and out of shaft 204 and/or connector assembly 214. Snare loop 210 is shown deployed in FIG. 2, and may be configured to be fully received within connector assembly 214 and/or shaft 204, or may be configured to be partially received within connector assembly 214 and/or shaft 204 when actuator 249 is pulled proximally by an operator. By moving actuator 249 longitudinally (distally or proximally), an operator may adjust the deployed size of snare loop 210. Cord 220 may extend from distal portion 206 to handle 202 and the positioning of cord 220 may allow an operator to pull cord 220 proximally during operation.

Figure 3A:
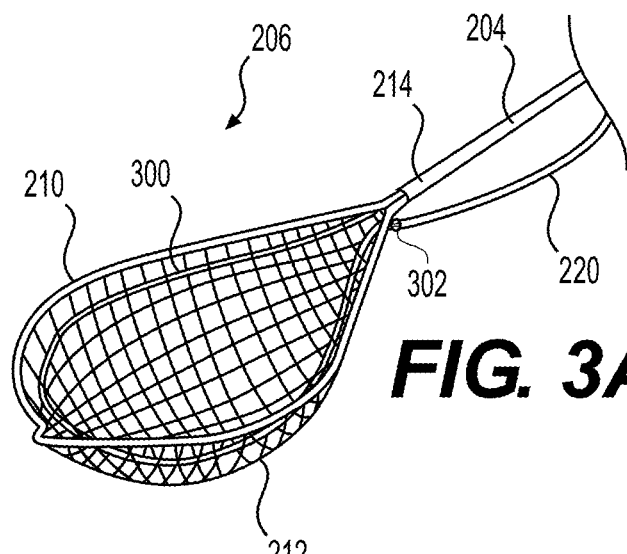
FIG. 3A illustrates a perspective view of a distal portion of the exemplary medical device in FIG. 2, according to aspects of this disclosure.

Cord 220 may be coupled to net 212 and may include a knot (e.g., a slip knot) 302 (FIG. 3A) tied at a proximal portion of snare loop 210 (when snare loop 210 is in the deployed, ready-to-capture configuration shown in FIG. 3A). In some examples, cord 220 may be coupled to net 212 by weaving cord 220 through holes of net 212, glued or otherwise adhered to net 212, and/or fastened to net 212 via one or more fasteners (e.g., stapled or clipped). FIG. 3A shows an exemplary distal portion 206 of medical device 200 with cord 220 weaved through net 212 to couple cord 220 to net 212. Cord 220 may be a string, wire, suture, line, or any other suitable rope known in the art. In some examples, slip knot 302 may extend around a proximal portion of snare loop 210 (not shown). In other examples, slip knot 302 is position proximate to net 212 and does not extend around a proximal portion of snare loop 210, such that slip knot 302 is positioned spaced apart from (above or below) snare loop 210 (shown in FIG. 3A). Slip knot 302 may be configured to allow an operator to pull cord 220 proximally and configured to prevent separation of cord 220 from net 212. For example, when an operator pulls cord 220 proximally, cord 220 may gather net 212 into a bundle and form an enclosed (or partially-enclosed) pouch with net 212, securing any captured items or material (e.g., a polyp, stone, or other object) within the pouch. Slip knot 302 may allow cord 220 to be pulled proximally to bring portions of net 212 together and prevent tissue or other material gathered within net 212 from moving out of net 212. Although slip knot 302 is shown in FIG. 3A, other fastening mechanisms may be used to prevent separation of cord 220 from net 212 while allowing proximal movement of cord 220, such as a spring biased connector or other fastening mechanism known in the art.

Net 212 may be fixedly coupled to snare loop 210 via glue, fasteners, or other adhesives/mechanisms known in the art. In some examples, net 212 may be coupled to snare loop 210 via coating or enveloping snare loop 210 with a bonding material, and then coupling a plurality of stands of net 212 to the bonding material. In some examples, portions of net 212 are embedded in the bonding material. Cord 220 may extend circumferentially around net 212, may be coupled to portions of net 212 proximate to snare loop 210, and may form a loop portion 300. By coupling cord 220 to net 212 proximate to snare loop 210, a sufficient amount of net 212 may be positioned on an opposing side of net 212 from snare loop 210 (either above or below cord 220) and available to collect tissue. Tissue may be transported in net 212 when cord 220 is pulled proximally to collect portions of net 212 together and form a bag or pouch assembly shown in FIG. 3B.

Connector assembly 214 may provide a mechanism to couple drive wire 408 to snare loop 210. Connector assembly 214 may be cylindrical and may be longitudinally aligned with shaft 204. In some examples, connector assembly 214 may be integral with shaft 204. Connector assembly 214 may be configured to provide a mechanism for the operator to adjust the size of the deployed snare loop 210 (e.g. change the circumference of the snare loop 210 via actuator 249), and provide a mechanism to detach snare loop 210, net 212, and cord 220 from shaft 204. In some examples, connector assembly 214 may be configured to decouple from shaft 204 when a user pulls drive wire 408 proximally with at least a threshold level of force. In other examples, handle 202 may include an actuator (separate from actuator 249) and connector assembly 214 may be configured to decouple from shaft 204 when the actuator is actuated (e.g., a button is pressed or a lever is pulled). Connector assembly 214 will be discussed in further detail below in relation to FIGS. 4 and 5.

Figure 3B:
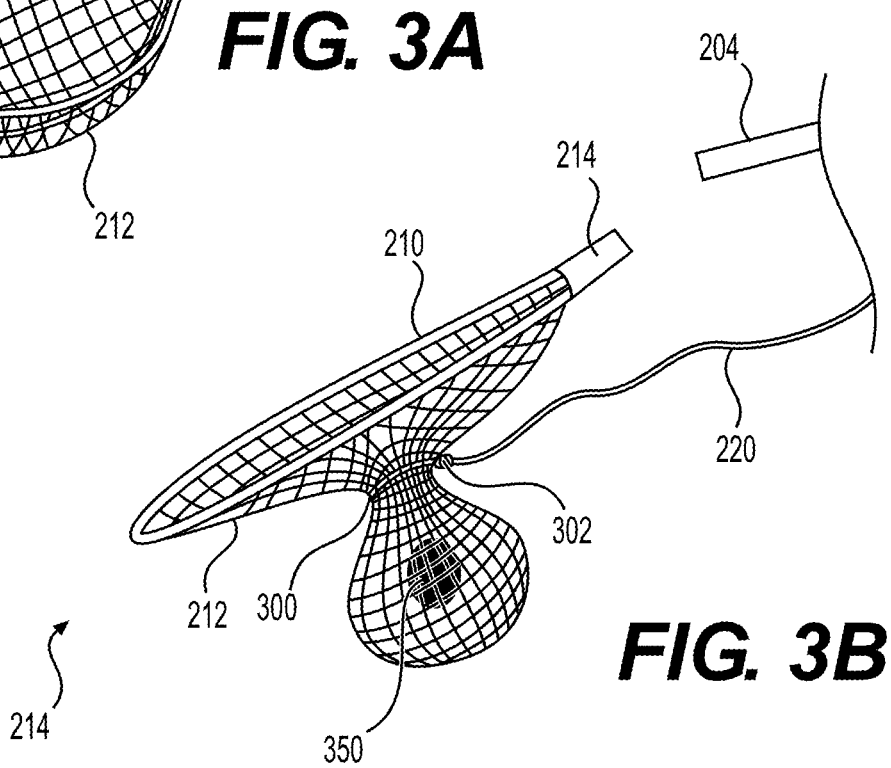
FIG. 3B illustrates a perspective view of a distal portion of the exemplary medical device in FIG. 2, according to aspects of this disclosure.

FIG. 3B shows snare loop 210 after a user has pulled cord 220 to tighten portions of net 212 together. As shown in FIG. 3B, cord 220 enables a user to pull cord 220 to bunch or sync portions of net 212 together and form a bag with net 212 around tissue (or object) 350. Snare loop 210 is decoupled from shaft 204 in FIG. 3B, and may be pulled proximally via cord 220 without moving shaft 204. Slip knot 302 is positioned away from (above or below) snare loop 210 proximate to net 212. Since loop 300 of cord 220 is coupled to portions of net 212 (e.g., weaved through holes of net 212), portions of net 212 are brought together when a user pulls cord 220 proximally.

In operation of medical device system 100, a user may first insert endoscope 101 into a body of a patient and position distal portion 108 proximate to a target area within the patient's body. A user may visualize the target area using a camera 105 of endoscope 101. The user may then insert distal portion 206 of medical device 200 through working channel 106 until distal portion 116 exits a distal opening of working channel 106. In other examples, a user may position medical device 200 within working channel 106 prior to insertion of endoscope 101 into the body of the patient. Once distal portion 206 exits working channel 106 and is positioned proximate to the target area, a user may move actuator 249 proximally or distally relative to body 224 of handle 202 to open and close snare loop 210. The user may then position net 212 around tissue and at least partially close snare loop 210 by pulling actuator 249 proximally. Once snare loop 210 is closed, the user may then pull cord 220 proximally to bring portions of net 212 together to form a bag with net 212 holding the tissue. The user may then pull actuator 249 further proximally to release snare loop 210 from shaft 204 via connector assembly 214 decoupling from shaft 204. Once snare loop 210 is released, the user may remove snare loop 210 from the body of the patient by pulling cord 220 proximally, and then may continue operating on patient using endoscope 101. Once treatment of the patient is completed, the user may fully remove medical device system 100 from the patient's body.

Figure 4:
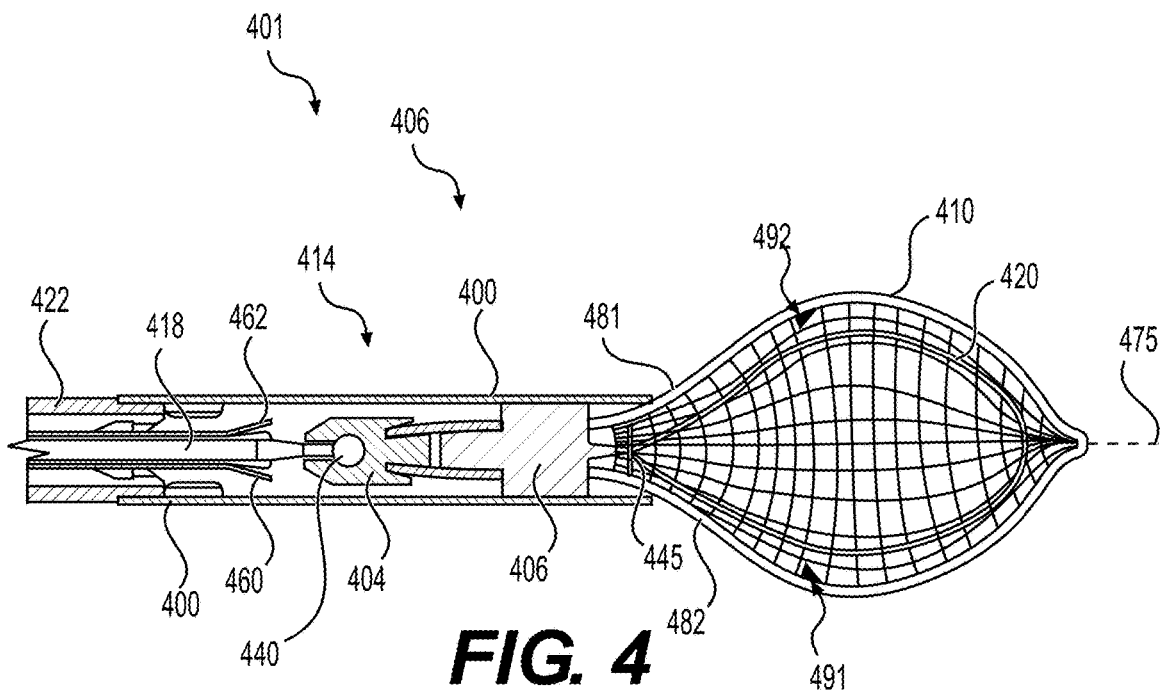
FIGS. 4-5 illustrate a distal end of a medical device with portions shown in cross-section, according to aspects of this disclosure.

FIG. 4 illustrates a distal portion 406 of a medical device 401 including snare loop 410, cord 420, connector assembly 414, and drive wire 418. Medical device 401, and any of its components, may include any of the features described herein in connection with medical device 101. FIG. 4 shows a more detailed view of an exemplary decoupling mechanism generally referred to in the previous figures. Medical device 401 may include a handle assembly identical to handle 202, and specifically medical device 401 may include an actuator 249. Connector assembly 414 is disposed at the distal portion of medical device 401, and contains a mechanism that converts the proximal and distal movement of control wire 418 into the actions necessary to actuate (e.g. expand/contract) and release snare loop 410. Some of the components of the connector assembly 414 include a capsule 400 which provides a structural shell for the connector assembly 414, snare loop 410 which moves between expanded and contracted positions, a bushing 422 attached to the distal end of the control wire 418, and a yoke 404 adapted to connect the capsule 400 to the control wire 418.

As depicted in FIG. 4, the proximal end of the capsule 400 slides over the distal end of the bushing 422. A locking arrangement between these two components is provided by tabs on capsule 400, which lock into bushing 422 so that mechanical integrity is temporarily maintained between the capsule 400 and the bushing 422. Within capsule 400 are a yoke 404 and a tension member 406 which transmit forces applied by the control wire 418 to snare loop 410. A ball 440 formed at the distal end of the control wire 418 is mated to a receiving socket formed at the proximal end of the yoke 404. In some examples, tension member 406 is received in yoke 404, so that the two components are releasably connected to one another. Snare loop 410, while in a closed or collapsed configuration, may be partially contained within the capsule 400 to prevent outward expansion of snare loop 410 from a central longitudinal axis 475 of device 401. Each proximal arm 481, 482 of snare loop 410 may extend through and be coupled to the tension member 406, and may have a proximal end which slips under a yoke overhang, to further control movement of the snare loop 410.

FIG. 4 shows a view of medical device 401 with snare loop 410 in an open configuration. The open configuration is obtained when ball 440 of the control wire 418 pushes the assembly containing the yoke 404 and the tension member 406 distally, sliding snare loop within and ultimately distal to the capsule 400. Snare loop 410 may be materially biased toward the open position and revert to this position whenever snare loop 410 is not constrained by the capsule 400. Snare loop 410 may include proximal arms 481, 482 that extend within capsule 400. In some examples, tabs 445 provide a cam surface, and the proximal arms 481, 482 of snare loop 410 act as cam followers, being deflected by the tabs 445. In addition, the folding tabs 445 may also provide a distal stop for the tension member 406, to retain tension member 406 within the capsule 400.

When the actuator 249 is moved proximally by the user, the yoke 404 and tension member 406 within the capsule 400 also moves proximally and snare loop 410 is withdrawn within the capsule 400. As proximal arms 481, 482 move proximally within the capsule 400, clip stop shoulders (CSS) 491, 492 contact a distal portion of the capsule 400, for example, the folded tabs 445. CSS 491, 492 may be rigid protrusions that extend radially inward towards a center of snare loop 410, may be triangular or any other suitable shape, and may be configured to engage with tabs 445. During contraction of snare loop 410, the interaction of the CSS 491, 492 with the capsule 400 provides to the user a first tactile feedback in the form of increased resistance to movement of sliding actuator 249. This feedback gives to the operator a positive indication that further movement of the handle control will cause the snare loop 410 to be detached from the connector assembly 414. The operator may then decide whether the current position of the snare loop 410 (e.g., within the body) is acceptable or not. If the position is acceptable, the operator can release snare loop 410 from a proximal portion of connector assembly 414 (and the body of medical device 401) by continuing to move actuator 249 with increased proximal pressure to cause the snare loop 410 to close. If not, the operator can move actuator 249 distally to re-open snare loop 410 and extend snare loop 410 out of the capsule 400, reposition the snare loop 410, and repeat the above steps to close snare loop 410 at a more appropriate location.

When the user determines that snare loop 410 is positioned correctly, the proximal pressure on actuator 249 may be increased to continue detachment of the snare loop 410 from connector assembly 414. As the proximal tension on actuator 249 is increased, control wire 418 pulls the yoke 404 proximally, away from the tension member 406. The tension member 406 is firmly attached to the proximal arms 481, 482 which are prevented from moving proximally by the interaction of the CSS 491, 492 with the folded tabs 445. If sufficient pulling force is applied to the yoke 404, tension member 406 may yield and lose integrity and/or lose connection with the yoke 404. In other words, after a sufficient proximal force, yoke 404 will decouple from tension member 406. This can occur because, in some examples, the tension member 406 is formed of a material with a lower yield strength than the material of the yoke 404.

The force required to decouple the tension member 406 from the yoke 404 may be tailored to achieve a desired feedback that can be perceived by the user. The minimum force required to break the tension member 406 free of the yoke 404 may be selected so that a tactile feedback is felt by the user, to prevent premature release of snare loop 410 while a maximum force may be selected so that other components of the linkage between actuator 249 and proximal arms 481, 482 do not fail before tension member 406 and yoke 404 disconnect from one another. In one exemplary embodiment, the tension force necessary to disconnect the two components may be in the range of about 4 lbf to about 12 lbf, although these values are not limiting. This range may vary depending on the size of the device and the specific application. To obtain this force at the interface of yoke 404 and tension member 406, a larger force may be applied by the user at actuator 249, since friction within the device may cause losses along the long flexible shaft.

When yoke 404 decouples from tension member 406, several events take place within medical device 401 nearly simultaneously. More specifically, the yoke 404 is no longer constrained from moving proximally by the CSS 491, 492 abutting the capsule 400. Thus, yoke 404 travels proximally until it comes to rest against a distal shoulder of bushing 422. The tension member 406 is not affected by this movement since it is no longer connected to the yoke 404.

A further result of moving the yoke 404 against a distal shoulder of the bushing 422 is that the distal end of a wire stop 460 is placed near a proximal bushing shoulder of bushing 422. Flared fingers 462 located at the distal end of the wire stop 460 are compressed as they pass through the bushing 422, but return to their normally biased open position after moving past a proximal bushing shoulder of bushing 422. Further distal movement of actuator 249 is thus prevented because the fingers 462 of wire stop 460 would abut against the proximal bushing shoulder of bushing 422. This abutment prevents connector assembly 414 from being pushed away from the bushing 422 before the ball 440 is separated from the control wire 418, as will be described below.

The wire stop 460 may include a tube with a first slotted and flared end attached to the control wire 418 by conventional mechanisms. The slots imparts flexibility to the control wire 418 so it can easily pass through the central lumen of the bushing 422. Flared fingers 462 are formed by the slots, and engage the proximal bushing shoulder. The wire stop 460 may include a material that is biocompatible and that has enough resilience so that the fingers 462 re-open after passage through the bushing 422. For example, stainless steel may be used for this application.

In at least some examples, the user receives both tactile and auditory feedback as the connector assembly 414 is deployed and released. The separation of the tension member 406 from the yoke 404 may produce a clicking noise and a tactile feel that is perceptible while holding handle 202.

The change in axial/longitudinal position of actuator 249 is thus augmented by the changes in resistance to its movement and by the clicking sound and tactile feedback through the start and stop of the movement. As a result, the user may always be aware of the status of the connector assembly 414, and the inadvertent release of snare loop 410 in an incorrect location is less likely. It will be apparent to those of skill in the art that the order of components (e.g., male and female connectors in the device may be reversed or changed without affecting the operation of the device.

Figure 5:
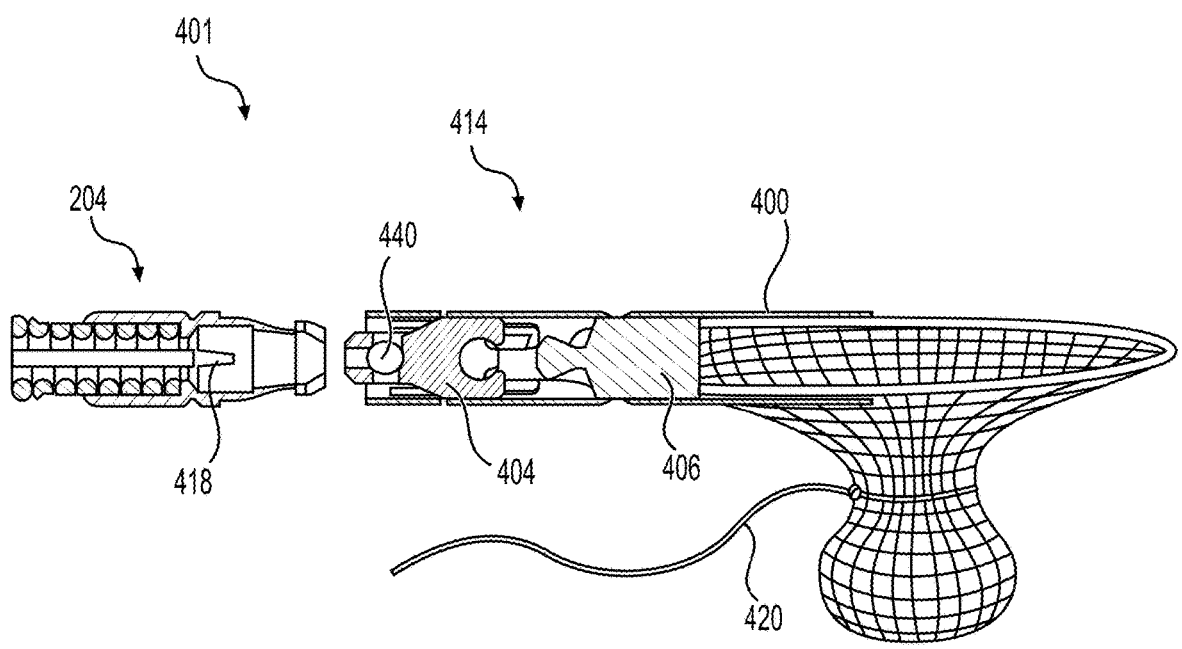

FIG. 5 depicts a configuration where connector assembly 414 has separated from a remainder of the medical device 401. The control wire 418 may be designed so that it separates from the end ball 440 only after a predetermined tension is applied to control wire 418. In other words, the ball 440 is configured to yield and separate from the body of the control wire 418 when a tension applied to control wire 418 reaches and/or exceeds a pre-set level.

As the ball 440 detaches, actuator 249 bottoms out at the proximal end of the handle 202, such that a full stroke of the handle assembly is reached. The tension required to cause the ball 440 to release from control wire 418 may be any suitable value. However, this tension force may be greater than the tension force required for the tension member 406 to separate from the yoke 404. If this condition is not satisfied, a situation may occur where the connector assembly 414 is locked in place, but cannot be released from medical device 401.

Once the ball 440 has separated from the remainder of the control wire 418, the user may pull cord 420. As this is done, the yoke 404 is retained within the capsule 400 by the spring and frictional forces of various features of the capsule 400, such as the capsule tabs. The user may then remove snare loop 410 including yoke 404, tension member 406, and capsule 400, from the patient, by pulling cord 420 proximally. Further description and additional embodiments of connector assemblies similar to connector assembly 414 may be found in U.S. Pat. No. 8,062,311, issue on Nov. 22, 2011, which is incorporated by reference herein in its entirety. Any of the clip assemblies or aspects of clip assemblies disclosed in the '311 patent application may be used as connector assemblies or other features in any of the medical devices disclosed herein.

In other examples, after decoupling of snare loop 210 from shaft 204, the proximal end of cord 220 could be tied off or otherwise secured at the proximal end of endoscope 101 with suture clips or other locking mechanisms. This would allow the captured material to remain trapped, while also keeping the material and net 212 out of direct view of camera 105, enabling a user to continue operating with endoscope 101.

In some examples, multiple medical devices 200 may be used with endoscope 101, and the user may snare tissue and remove multiple snare loops 210 from a patient's body during a procedure without removing endoscope 101. In some examples, snare loops 210 may be removed by pulling cord 220 proximally and moving snare loops 210 proximally outside of endoscope 101, and/or snare loops 210 may be removed from patient by puling cord 220 proximally through a working channel of endoscope 101.

It also should also be understood that one or more aspects of any of the medical devices, systems, and methods described herein may be used for cutting, capturing, holding, dissecting, treating, or ablating tissue in any part of the human body. For example, any of the medical devices described herein may be used in medical procedures such as for Endoscopic Submucosal Dissection (ESD), cancer treatment, and/or other procedures where removal of the type of tissue is needed.

Various aspects discussed herein may help reduce procedure time, increase tissue treatment effectiveness, reduce the risks to the subject, etc.

Although the exemplary embodiments described above have been disclosed in connection with medical devices for manipulating and capturing human tissue through the working channel of a medical device, a natural orifice, or by incision, a person skilled in the art will understand that the principles set out above can be applied to any medical device or medical method and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of the this disclosure and can be envisioned and implemented by those of skill in the art.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

While principles of the disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

Other exemplary embodiments of the this disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the this disclosure as defined by the following claims.

We claim:

1. A method of retrieving an object from a body, the method comprising:
    inserting a medical device with a working channel into the body;
    extending a sheath, an expandable wire loop, a net coupled to the expandable wire loop, and a fastening mechanism coupled to the net, through the working channel, and distally of the medical device, wherein the expandable wire loop further comprises a capsule;
    placing the net around the object;
    actuating an actuator on a handle, wherein the actuator is moveable in a proximal or a distal direction relative to a body of the handle, and wherein, after placing the net around the object, the actuator is moved proximally to at least partially close the expandable wire loop;

wherein, after placing the net around the object, moving the actuator further proximally moves the expandable wire loop partially within the capsule;

applying a pulling force on the fastening mechanism to close at least a portion of the net around the object; and decoupling the expandable wire loop, the net, and the object from the sheath by actuating a drive wire coupled to the expandable wire loop, wherein the drive wire is configured to move the expandable wire loop relative to the sheath.

2. The method of claim 1, wherein the net has an open end and a closed end, wherein the open end is at least partially circumscribed by the expandable wire loop, wherein the closed end is spaced apart from the open end, and wherein, prior to inserting the medical device into the body, the fastening mechanism is coupled between the open end and the closed end of the net.

3. The method of claim 1, wherein, after the expandable wire loop is partially within the capsule, continuing movement in the proximal direction produces a first feedback indicating that further proximal movement decouples the expandable wire loop from the sheath.

4. The method of claim 3, wherein continuing movement in the proximal direction after the first feedback decouples the expandable wire loop, the net, and the object from the sheath.

5. The method of claim 4, wherein decoupling the expandable wire loop from the sheath is configured to produce a second feedback indicating decoupling has occurred.

6. The method of claim 1, wherein the fastening mechanism is a cord, and wherein the pulling force on the fastening mechanism is a proximal force.

7. The method of claim 1, wherein, upon closing the net, the net forms a substantially-enclosed bag or sac.

8. The method of claim 1, further comprising:
removing the expandable wire loop, the net, and the object from the body separately from the medical device.

9. A method of retrieving an object from a body, the method comprising:
inserting a medical device with a working channel into the body, wherein the medical device includes a handle with an actuator;

extending a sheath, a snare loop, a net coupled to the snare loop, and a cord coupled to the net, through the working channel, and distally of the medical device, wherein a drive wire is coupled to the snare loop, and wherein moving the actuator tensions the drive wire to move the snare loop relative to the sheath, and wherein the snare loop further comprises a capsule;

positioning the net around the object, wherein the actuator is moveable in a proximal direction or in a distal direction relative to a body of the handle, wherein after placing the net around the object, the actuator is moved proximally to at least partially close the snare loop;

wherein, after placing the net around the object, moving the actuator further proximally moves the snare loop partially within the capsule;

moving the actuator to at least partially close the snare loop;

applying a force on the cord to close at least a portion of the net around the object; and decoupling the snare loop, the net, and the object from the sheath by moving the actuator to reach a threshold level of force.

10. The method of claim 9, wherein after the snare loop is partially within the capsule, the actuator is configured to reach the threshold force by continuing proximal movement.

11. The method of claim 9, wherein the force applied on the cord is a proximal force.

12. The method of claim 9, wherein, upon closing the net, the net forms a substantially-enclosed bag or sac.

13. A method of retrieving an object from a body, the method comprising:
inserting a medical device with a working channel into the body, wherein the medical device includes a handle with an actuator;

extending a sheath, a snare loop, wherein the snare loop further comprises a capsule, a net coupled to the snare loop, and a cord coupled to the net, through the working channel, and distally of the medical device;

positioning the net around the object;

moving the actuator in a proximal direction relative to a body of the handle, wherein after placing the net around the object, the actuator is moved proximally to at least partially close the snare loop, wherein, after placing the net around the object, moving the actuator further proximally moves the snare loop partially within the capsule;

applying a proximal force on the cord to close at least a portion of the net around the object; and decoupling the snare loop, the net, and the object from the sheath by moving the actuator further proximally.

* * * * *